United States Patent [19]

Gelo et al.

[11] Patent Number: 4,687,500

[45] Date of Patent: Aug. 18, 1987

[54] METHOD FOR MANUFACTURING AN ION-SENSITIVE ELECTRODE

[75] Inventors: Mark A. Gelo, Concord; Moshe J. Hirshberg, Brookline, both of Mass.

[73] Assignee: Orion Research Inc., Cambridge, Mass.

[21] Appl. No.: 812,743

[22] Filed: Feb. 13, 1986

Related U.S. Application Data

[62] Division of Ser. No. 647,599, Sep. 5, 1984.

[51] Int. Cl.[4] ............................................. C03B 23/20
[52] U.S. Cl. .......................................... 65/36; 65/57; 65/155
[58] Field of Search ..................... 204/416, 419, 420; 65/36, 57, 152, 155

[56] References Cited

U.S. PATENT DOCUMENTS

| | | | |
|---|---|---|---|
| 2,512,971 | 6/1950 | Roovers | 65/36 |
| 3,448,032 | 6/1969 | Settzo et al. | 204/420 X |
| 3,718,567 | 2/1973 | Haddad et al. | 204/420 X |
| 3,741,884 | 6/1973 | Deushane et al. | 204/420 |
| 3,806,440 | 4/1974 | Gray et al. | 204/420 |
| 3,853,731 | 10/1974 | Gray et al. | 204/420 |
| 3,876,408 | 4/1975 | Geyer | 65/36 |
| 3,876,409 | 4/1975 | Sangermano et al. | 65/40 |
| 4,485,001 | 11/1984 | Harman, III et al. | 204/420 X |

Primary Examiner—John F. Niebling
Assistant Examiner—Nam X. Nguyen
Attorney, Agent, or Firm—Cesari and McKenna

[57] ABSTRACT

The body of an ion-sensitive electrode is formed from a bulb (32) of an ion-selective material that is transparent to infrared radiation. A glass tube (12) made of material that absorbs infrared radiation is inserted into the bulb, and a source (15) of infrared radiation is focused through the bulb (32) onto the end of the tube (12) on which the bulb (32) rests. The resultant heating causes the tube and the bulb to fuse together, and the portion of the bulb outside the tube is then removed to result in an electrode body (FIG. 4).

7 Claims, 5 Drawing Figures

METHOD FOR MANUFACTURING AN ION-SENSITIVE ELECTRODE

This is a division of application Ser. No. 647,599 filed Sept. 5, 1984.

FIELD OF THE INVENTION

The invention relates to ion-sensitive electrodes and comprises a flat surface electrode formed from a portion of a bulb of ion-selective membrane material fused to the end of a tube through the use of radiation. It is particularly useful in forming low resistance electrodes from high resistivity material.

BACKGROUND OF THE INVENTION

Ion-sensitive electrodes measure the activity of ions in solution (both aqueous and non-aqueous) and are well known in the art of analytical chemistry. One example of such a measurement is pH, which is a measure of the activity of hydrogen ions in solution, and is an important parameter for many chemical processes. Another example is the measurement of sodium ions in foods or biological fluids.

Ion-sensitive electrodes are commonly formed from a tubular shell having one end sealed with an ion-selective membrane. The membrane is selectively permeable to ions of one type, while excluding others present in the sample solution. Inside the tube there is a means for providing a fixed potential, either a solution of fixed composition or a solid conductor in contact with the membrane. The potential across the membrane, measured from the internal contact, through the sample to a second reference contact provides a measure of the sample ion activity.

Ion-selective membranes are most commonly formed with either a bulbous or a flat shape. For membranes formed in the glassy state, bulbous-shaped electrodes are more readily formed than flat-membrane electrodes, and are suitable for measurements of liquid samples where there is a significant quantity of liquid available for measurement. Flat-membrane electrodes, in contrast, are desirable, or even required, for measuring samples where there is a limited quantity of material available, and for measuring moist solids where the membrane must be pressed against the sample without immersion in it.

The membranes used for ion-sensitive electrodes typically present a high input impedence to the measuring instrument, e.g., up to 1000-20000 megohms. This impedence limits the accuracy of measurements because of noise pickup in the electrode. In particular, the ion-selective membranes for pH-sensing electrodes are commonly formed from glass. In common pH-sensing glasses, high selectivity for a hydrogen ion is typically also accompanied by high resistivity, and thus the improved sensitivity otherwise obtainable from the material is masked by the increased noise pickup caused by the higher resistivity. This can be particularly a problem with flat surface membranes in which conventional manufacturing techniques place stringent limits on the extent to which the membrane thickness (and thus, its resistance for a material of given resistivity) may be controlled.

Flat-membrance surface ion-sensitive electrodes are commonly constructed by a dipping process in which a tubular section of glass is immersed in a molten bath of membrane material. A bead of molten material typically adheres to the end of the tubular section, and is fabricated into a flat membrane on cooling. The molten glass must have a coefficient of expansion closely matching that of the tube. If the coefficients of expansion of the tube and the molten glass differ greatly, either the tube or the membrane material will frequently crack upon cooling, due to differing rates of contraction. Further, the seal between the tube and the membrane glass is often irregularly formed and prone to failure. In addition, dipping processes are difficult to control for uniformity and repeatability of membrane thickness. Sample to sample thickness variations may lead to large variations in strength or electrical resistance.

Once the dipped tube has cooled, the pH glass may be ground to a desired thickness for the flat membrane required. Grinding is a time consuming process and results in a high percentage of defective electrode bodies due to accidental breaking of the thinned membrane material. Further the grinding process introduces microgrooves and stresses into the membrane. Impurities from the grinding material may also embed themselves into the areas that are ground and thereby distort membrane properties. Finally, there is a physical limit to the thickness to which one can grind a material, without breaking that material. The limitation is due to the impact nature of the grinding process and the brittle nature of membrane material. This limitation has prevented the use, in flat or substantially flat membranes, of low-sodium interference high-resistivity glass.

A need therefore exists for a new method of manufacturing electrode bodies which will allow for the development of improved electrodes utilizing improved materials and having none of the drawbacks of conventional electrodes.

SUMMARY OF THE INVENTION

The invention comprises an ion-sensitive electrode which is formed from a bulb of ion-selective membrane material, which is transparent to radiation, and a tube of radiation-absorptive materials. The bulb is rested upon the tube and the interface between the tube and bulb then irradiated so as to heat the tube to a molten state to therby secure bonding between the tube and a spherical section of the bulb. In particular, in the preferred embodiment, the assembly is irradiated with infrared radiation focused on the end face or 'lip' of the tube at the surface which contacts the bulb. This melts the tube wall to an extent sufficient to form a bond with the membrane without melting the membrane. Thereafter, the tube is slightly pressured with gas (e.g., a quick puff of air, such as is common in manual glassblowing techniques) while the interface is still molten to reduce bonding stresses.

In the preferred embodiment of the invention, the bulb is of a substantially larger diameter than the tube, e.g., two or more times as large. When a segment of the inner portion of the bulb is rested on the tube, the tube subtends a portion of the spherical surface of the bulb which varies relatively little in height with respect to the end face of the tube. For example, when the bulb diameter is twice that of the tube, the subtended portion of the membrane projects less than 14% of the tube diameter beyond the end face of the tube. The result is a membrane that is substantially flat.

An important consequence of this method of construction is that it permits the use of high-resistivity, low sodium error materials for the membrane, e.g. materials whose selectivity for hydrogen ion as opposed to sodium ion is of the order of $10^{13}$ or more and preferably as high as $10^{14}$ or more. This is because the glasses used for the membrane can be blown into structurally strong bulbs having cross sections thinner then those which can be found in conventionally constructed flat surface electrode membranes. Thus, while the resistivity of the material is higher, its resistance is lower due to the membrane's reduced thickness. For example, with the present techniques, a flat-membrane, low-interference, low resistance, pH electrode is formed from a glass bulb less than 0.025 inches thick and having a resistivity value greater then $10^5$ ohm-centimeters. The sensitivity of this electrode extends the useable response to values of pH=14.

BRIEF DESCRIPTION OF THE DRAWINGS

The foregoing and other features and advantages of the invention will be apparent from the following more particular description of the preferred embodiment of the invention, as illustrated in the accompanying drawings, in which like reference characters refer to the same parts throughout the different views. The drawings are not necessarily to scale, emphasis instead being placed upon illustrating the principles of the invention.

DETAILED DESCRIPTION OF THE INVENTION

Figure 1:
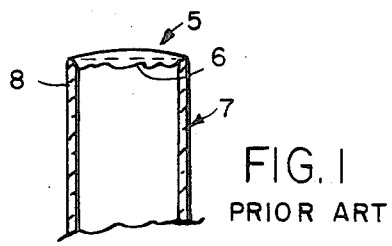
FIG. 1 is an expanded cross sectional view of a portion of an electrode formed by a dipping process. It depicts the prior art.

In FIG. 1, a typical flat membrane electrode formed by the usual dipping process characteristic of the prior art is shown. The membrane material 5 which is bonded to the tube 8 during the dipping process has an irregular contour on its inner surface 6. This irregular contour cannot be corrected by grinding and as a result, varies with each electrode manufactured. This results in a membrane of variable and high resistance and thus of adverse noise pickup characteristics.

Figures 2, 3:
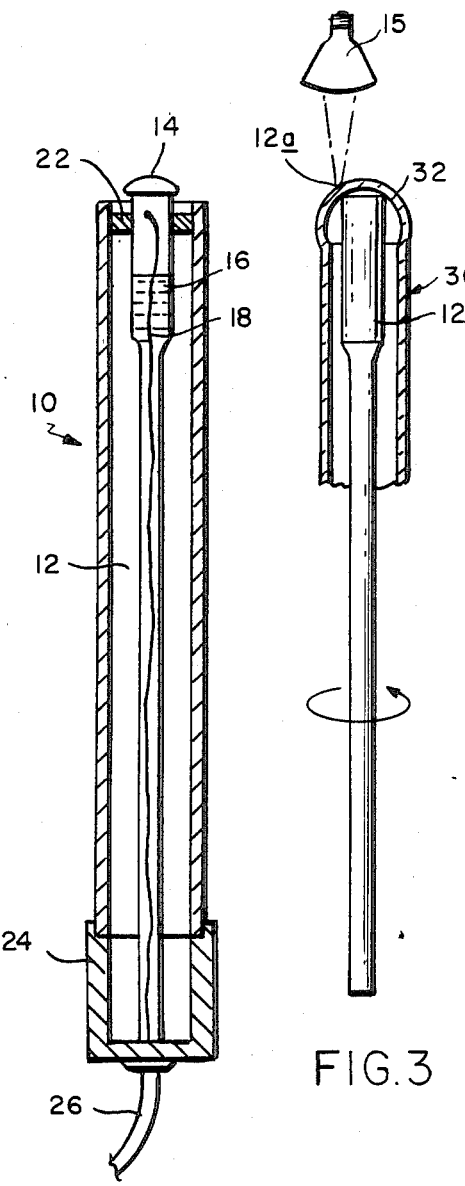
FIG. 2 is a partial cross-section view of an ion-sensitive electrode.
FIG. 3 is a view of the electrode body prior to membrane bonding in which an infrared light source is shown schematically.

An improved ion sensitive electrode 10 is shown in FIG. 2. The electrode 10 has an electrode body 12 of generally tubular shape having one end thereof sealed by a substantially flat membrane 14. The electrode body is formed from an energy absorbent (preferably infrared-absorbent) glass tube and a bulbous membrane preform as detailed below. Use of the bulbous preform for the electrode body permits the manufacture of flat surface electrodes with high resistivity membrane materials. As is common in ion sensitive electrodes, an internal filling solution 16 provides an electrically conductive path between the membrane and an electrode element 18 which measures a potential difference caused by a change in the ion concentration in the sample filling solution.

The membrane 14 is preferably formed from a pH or other ion selective glass. Such glasses are typically a mixture of several oxides including $Li_2O$, $Cs_2O$, $La_2O_3$, $CaO$, and $Na_2O$. A variety of other similar constituents have also been used. Further, the membrane 14 is formed of a thin, substantially flat material, preferably less than 0.025 inches thick, and as thin as 0.005 inches. This is a far thinner membrane section than previously could be used on flat membrane ion exchange electrodes, and therefore can be formed of low-interference materials such as low-sodium interference glasses having resistivities greater than $10^5$ ohm-centimeters. Although such materials have high resistivities, preferably about $2.5 \times 10^6$ ohm-centimeters, the reduced membrane thickness offsets the increased resistivity, and results in a membrane with overall moderate resistance. Accordingly, electrical noise pick up is significantly reduced and a more accurate measurement of an increased pH range is obtained. For example, flat-membrane electrodes capable of measuring pH over the range of 0 to 14 can produced by the present process.

In order to protect the glass electrode body 12 from accidental breakage during use, an outer protective tube 20 is placed around it. This outer tube is preferably constructed of resilient plastic and is attached to the membrane end of the inner tube 12 by means of a shock absorbing rubber gasket 22. A cap 24 and lead wires 26 are attached at the remote end of the electrode body to complete the structure.

Figure 3A:
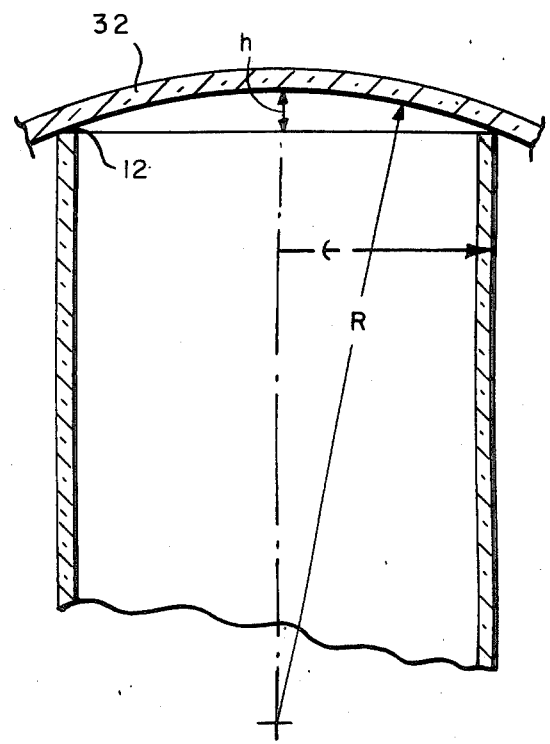
FIG. 3A is an enlarged view of a portion of FIG. 3A.

The electrode of FIG. 2 is manufactured as follows: Referring to FIG. 3, a preform 30 is formed in the shape of a cylindrical tube having a bulbous head 32 with a diameter substantially larger than that of the end of body 12 on which the membrane is to be formed. As mentioned above, for pH electrodes, the preform 30 may advantageously be made from a low sodium-interference, high resistivity material which is transparent to infrared radiation. Further the bulb 32 is formed to a reduced wall thickness, e.g. on the order of 0.005 inches. The wall thickness of the bulb is easily controlled by varying the bulb radius (R) for a given amount of glass. The flatness of the bulb is controlled by selection of the ratio of bulb diameter to tube diameter. In particular, with reference to FIG. 3A, the departure 'h' of the bulb membrane from perfect flatness (h=0) can readily be computed as $h = 1 - [1 - \cos(\sin^{-1} a)]/a$, where r is the tube radius and a is the ratio, r/R, of tube radius to bulb radius. For a ratio of a=0.5, h=0.268r, that is, the subtended portion of the membrane sealing, the tube departs from flatness by less than fourteen per cent of the tube diameter. For a=0.33, the departure is less than nine per cent.

Despite its limited thickness, the bulb is structurally quite strong and thus is relatively stable and easy to handle. Further, the slightly arched shape is believed to contribute to the strength, since glass is stronger in compression than tension. A flat plate of similar thickness would be extremely fragile and quite difficult to handle. Further, the bulb has a relatively constant wall thickness so that membrane thickness, and therefore resistance, may be closely controlled.

The preform 30 is placed over one end of the electrode body 12, with the bulb resting directly on the edge of the tubular body 12. As mentioned above, the body 12 preferably comprises an infrared absorbent glass. Infrared absorbent glass is commonly called "green glass"; examples include 'SRI' glass and 'STI' glass manufactured by the Nippon Electric Glass Co., Ltd., 1-1 KAKUDA-CHO, KITADU, Osaka, Japan, as well as certain glasses manufacturd by the Schoot Company, e.g. Schott No 4840E glass.

The next step in the manufacture of the electrode body is to focus a beam of radiation, such as from an infrared source 15, slightly above the interface between the bulb 32 and the end 12a of body 12. The light passes through the infrared transparent bulb 32 with little absorption and thus little heating, and evenly heats the 'lip' of the infrared absorptive glass tube 12 at its area of contact with the membrane. The tube is rotated at this time in order to keep the heating uniform. The radiation is then brought to a focus at the interface so as to melt the lip of the tube to thereby enable fusing of the tube to the membrane. The infrared energy is then removed (e.g., the source is turned off). It should be noted that the melting point of the glass of the tube is lower than that of the membranous bulb. If this were not the case, the thin bulb might soften and collapse during the fusing process.

Figure 4:
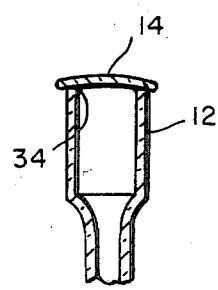
FIG. 4 is an expanded cross-section of the operational end of the ion-sensitive electrode of FIGS. 2 and 3.

As the assembly begins to cool, it is useful to slightly pressurize the air space within the tubular section 12 in order to promote formation of a uniform seal joint 34 (FIG. 4) between the glass electrode body and the membrane 14. This slight pressurization of the air space also eliminates internal stresses created by the fusing process in the membrane 14 and the joint 34.

As the fused assembly cools, the remainder of the membrane material tends to crack and fall away. The fused assembly then need only be polished at any ragged edges about the periphery of the membrane 14 before it is ready for use. The main section of the membrane material, which is thin and unsupported, does not need to be polished or ground. The electrode body 12, with the fused membrane material 14 is then ready for final assembly and the electrode element 18 can be inserted into the body and terminated at the opposite end of the housing.

The improved ion-sensitive electrode made by the above process is capable of superior operation when compared with previous flat surface, ion-sensitive pH electrodes. The method of manufacture, as described above, permits virtually flat membrane wall thicknesses as low as 0.005 inches and therefore allows the use of much higher resistivity materials for flat membranes than those available previously. Thus, high performance materials, desirable for the reduced sodium interference effects which characterize them but hitherto contraindicated by their high resistivity which led to increased electerical noise pickup, can now advantageously be used to form pH electrodes operable over a wide pH range.

This process of manufacture also makes advantageous use of the highly uniform wall thicknesses that can be achieved in blowing glass bulbs. The bulb 32 of membrane material is blown to a uniform desired wall thickness; as a result the membrane formed on the tube 12 also possesses a uniform wall thickness. This avoids the undesirable electrode resistance variations discussed in reference to FIG. 1.

The membrane is also structurally improved by the use of this process. The uniform joint between the tube body 12 and membrane 14 is quite strong and less likely to separate than the joints formed by previous methods. Further, microscratches and stresses which are induced by conventional grinding of a membrane surface to the proper thicknesses for flat membranes are completely eliminated by this process. The membraneous bulb needs no further processing after its fusing to the tubular body of the electrode probe. This results in an improved membrane surface with less likelihood of electrode cracking.

Finally, it should be noted that the process used in the manufacture of this improved ion sensitive electrode substantially reduces the cost of manufacture. Since hand grinding and polishing is largely eliminated, the most time consuming and delicate operation in the construction of flat surface ion sensitive electrodes has been eliminated. Further, waste caused by membrane breakage during grinding and polishing is also eliminated.

While the invention has been particularly shown and described with reference to the preferred embodiment thereof, it will be understood by those skilled in the art, that various changes in form and detail may be made therein without departing from the spirit and scope of the invention as defined by the appended claims. It is possible, for example, to utilize other electromagnetic energy sources such as ultraviolet light to fuse the material of the body to the membrane material. Further, the materials used to construct the probe need not be limited to glasses: ceramic and epoxy materials have also been used in ion sensitive electrode devices with good results. In appropriate cases, an intermediate meltable bonding material, compatible with both the tubular wall material and the membrane material, may be used to effectuate the desired bond in cases where the membrane material and the tubular wall material may not themselves be sufficiently directly compatible.

What is claimed as new and desired to be secured by Letters Patent of the United States is:

1. For manufacturing an ion-sensitive-electrode body having a portion formed of an ion-selective membrane material, a method comprising the steps of:
    A. inserting an end of a tube, which tube consists essentially of material that absorbs radiation of a predetermined wavelength, into a bulb consisting essentially of an ion-selective membrane material that is substantially transparent to radiation of the predetermined wavelength so that the end of said tube contacts an inner surface of said bulb; and
    B. shining radiation of the predetermined wavelength through said bulb onto the end of said tube in contact with said bulb to fuse said end of said tube to the inner surface of said bulb.

2. The method of claim 1 wherein the predetermined wavelength lies in the infrared region.

3. The method of claim 1 wherein said bulb is less than 0.025 inch thick.

4. The method of manufacturing an electrode body of claim 1 further comprising the step of:
    slightly pressurizing said electrode body after fusing said tube to said bulb in order to eliminate internal stresses in said tube.

5. The method of manufacturing an electrode body of claim 1 wherein said ion-selective membrane material is selectively permeable to hydrogen ions.

6. The method of manufacturing an electrode body of claim 1 wherein said ion-selective membrane material comprises a limited portion of the surface of said bulb to thereby form a substantially flat surface.

7. The method of claim 6 wherein the said bulb has a radius of at least twice the radius of said tube.

* * * * *